United States Patent [19]

Raynaud et al.

[11] 4,029,650
[45] June 14, 1977

[54] NOVEL DERIVATIVES OF N-(3,4,5-TRIMETHOXY CINNAMOYL)PIPERAZINE AND THE PROCESS FOR PREPARING THEM

[75] Inventors: Guy M. Raynaud, Paris; Bernard M. Pourrias, Meudon-la-Foret; Claude P. Fauran; Michel J. Turin, both of Paris, all of France

[73] Assignee: Delalande S. A., Courbevoie, France

[22] Filed: Nov. 20, 1975

[21] Appl. No.: 633,932

[30] Foreign Application Priority Data

Nov. 20, 1974 France .................. 74.38203
Sept. 29, 1975 France .................. 75.29782

[52] U.S. Cl. .................. 260/240 J; 260/250 BN
[51] Int. Cl.² .............. C07D 241/02; C07D 403/06
[58] Field of Search .................. 260/240 J, 250 BN

[56] References Cited

UNITED STATES PATENTS

| | | | |
|---|---|---|---|
| 3,634,411 | 1/1972 | Fauran et al. | 260/240 J |
| 3,639,476 | 2/1972 | Eberle et al. | 260/250 BN X |
| 3,753,984 | 8/1973 | Fauran et al. | 260/240 J |

FOREIGN PATENTS OR APPLICATIONS 245,904 7/1963 Australia .................. 260/240 J Primary Examiner—Allen B. Curtis
Attorney, Agent, or Firm—Woodhams, Blanchard and Flynn

[57] ABSTRACT

Compounds having the formula

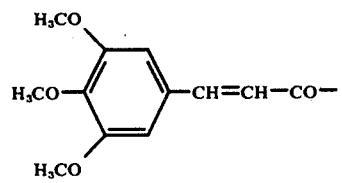

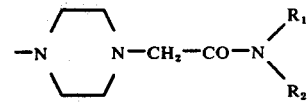

in which $R_1$ is alkyl having no more than 4 carbon atoms and $R_2$ is dimethoxyphenylethyl or

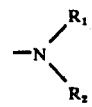

is piperidino, heptamethyleneimino or 1,2,3,4-tetrahydroisoquinolino. The compounds are prepared by condensing N-(3,4,5-trimethoxy cinnamoyl)N'-(carboxymethyl) piperazine with

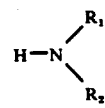

The compounds possess peripheral, coronary and cerebral vasodilatory properties and an antihypertensive property.

8 Claims, No Drawings

NOVEL DERIVATIVES OF N-(3,4,5-TRIMETHOXY CINNAMOYL)PIPERAZINE AND THE PROCESS FOR PREPARING THEM

U.S. Pat. No. 3,634,411 discloses derivatives of N-(3,4,5-trimethoxy cinnamoyl piperazine having the general formula (Io):

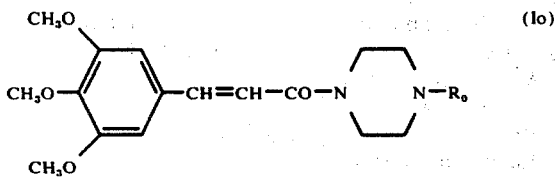

in which $R_0$ represents a chain of formula

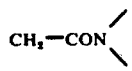

where the nitrogen atom is secondary or tertiary.

The present application relates to derivatives of piperazine within the framework of formula Io and having the general formula I:

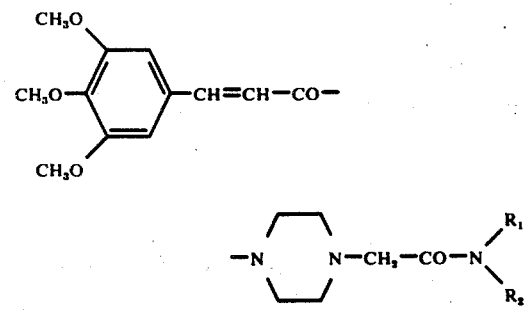

in which the symbol

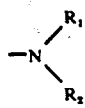

designates
either a tertiary amino group in which $R_1$ represents an alkyl radical containing no more than four carbon atoms and $R_2$ is a dimethoxyphenyl ethyl group;
or a piperidino, a heptamethylenimino or a 1,2,3,4-tetrahydro isoquinolino radical.

The process of preparation according to the present invention consists in condensing N-(3,4,5-trimethoxy cinnamoyl) N'-(carboxymethyl)piperazine of formula II:

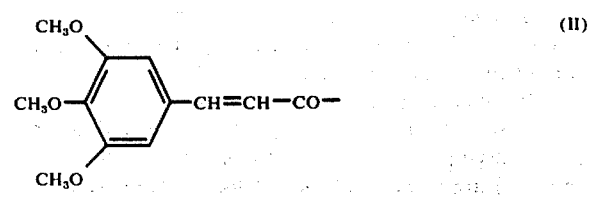

with a secondary amine of formula III:

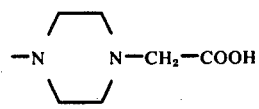

in which $R_1$ and $R_2$ have the same significance as in formula (I), by means of butyl chloroformate of formula IV:

The operation is carried out in the presence of triethylamine and in a tetrahydrofuran medium.

The corresponding oxalate or maleate can then be prepared by salifying the base by means of oxalic or maleic acid in an acetone or an ethyl acetate medium.

The following preparations are given as examples to illustrate the invention.

EXAMPLE 1:

N-(3,4,5-trimethoxycinnamoyl)-N'-(piperidino carbonyl methyl) piperazine maleate.

Code number 74 0479

To a solution of 0.15 mole of N-3,4,5-trimethoxy cinnamoyl-N'-(carboxymethyl) piperazine in 400 ml of anhydrous tetrahydrofuran, maintained at −10° C, is added 0.16 mole of triethylamine and 0.15 mole of n-butyl chloroformate. Then piperazine (0.3 mole) is added and it is left for three hours to return to room temperature. The medium is concentrated, and the precipitate filtered and washed with a solution of potassium hydroxide at 5%, then the compound obtained is recrystallised in isopropyl alcohol. Melting point: 172° C Yield: 44% Empirical formula: $C_{23}H_{33}N_3O_5$ The base obtained is salified in acetone solution by means of maleic acid and the resulting salt is recrystallised in alcohol at 96°. Melting point: 178° C
Yield: 79%
Empirical formula: $C_{27}H_{37}N_3O_9$
Elementary analysis:

|  |  | C | H | N |
|---|---|---|---|---|
| Calculated | (%) | 59.22 | 6.81 | 7.67 |
| Found | (%) | 59.06 | 6.76 | 7.78 |

EXAMPLE 2:

N-(3,4,5-trimethoxy cinnamoyl)-N'-(heptamethylenimino carbonyl methyl) piperazine oxalate Code number 74 0678

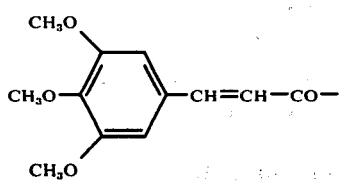

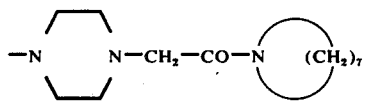

To a solution of 0.103 mole of N-(3,4,5-trimethoxy cinnamoyl)-N'-(carboxymethyl) piperazine in 250 ml of tetrahydrofuran, cooled to −10° C, was added 0.11 mole of triethylamine, then 0.103 mole of butyl chloroformate.

After contact at −10° C for 45 minutes, 0.206 mole of heptamethylenimine is added between −10 and 0° C. It is left to react for 4 hours and to return to room temperature. The precipitate formed is separated by filtration and the tetrahydrofuran is evaporated. The evaporation residue is treated with 150 ml of an aqueous solution of 5% potassium hydroxide. The precipitate formed of N-(3,4,5-trimethoxy cinnamoyl)-N'-(heptamethylenimino carbonyl methyl) piperazine is separated by filtration, purification being effected by recrystallisation in 200 ml of an isopropyl alcohol/isopropyl ether (10/90) mixture.

Melting point: 116° C
Yield: 50%
Empirical formula: $C_{25}H_{37}N_3O_5$
Elementary analysis:

|  |  | C | H | N |
|---|---|---|---|---|
| Calculated | (%) | 65.33 | 8.12 | 9.14 |
| Found | (%) | 65.47 | 8.28 | 9.39 |

The base obtained is salified in an ethyl acetate solution by the stoichiometric amount of oxalic acid and the resulting salt is purified by recrystallisation in ethanol.

Melting point: 212° C
Yield: 92%
Empirical formula: $C_{27}H_{39}N_3O_9$
Elementary analysis

|  |  | C | H | N |
|---|---|---|---|---|
| Calculated | (%) | 59.00 | 7.15 | 7.65 |
| Found | (%) | 58.94 | 7.11 | 7.38 |

EXAMPLE 3

N-(3,4,5-trimethoxy cinnamoyl)-N'-(1,2,3,4-tetrahydro isoquinolino carbonyl methyl)piperazine.

Code number 75 0001

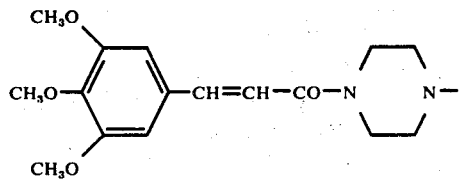

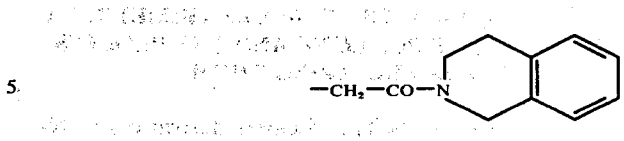

The method of operation is identical with that used in example 2, the secondary amine used being 1,2,3,4-tetrahydro isoquinoline.

The base obtained is purified by recrystallisation in an isopropyl alcohol/isopropyl ether (2/1) mixture.

Melting point: 152° C
Yield: 30%
Empirical formula: $C_{27}H_{33}N_3O_5$
Elementary analysis:

|  | C | H | N |
|---|---|---|---|
| Calculated (%) | 67.62 | 6.94 | 8.76 |
| Found (%) | 67.51 | 6.82 | 8.73 |

EXAMPLE 4

N-(3,4,5-trimethoxy cinnamoyl)-N'-[N''-methyl N''-(3,4-dimethoxy phenyl ethyl) aminocarbonyl methyl] piperazine.

Code number 75 0002

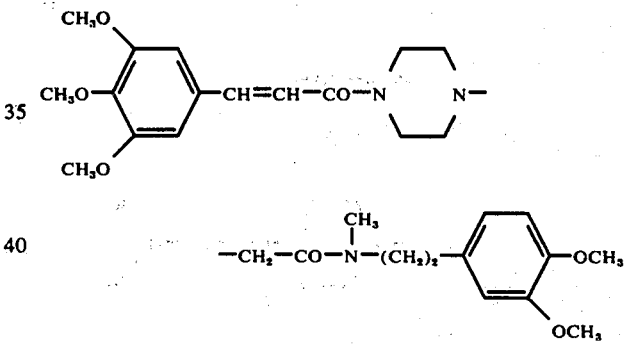

The method of operation is identical to that used in example 2, the secondary amine used being N-methyl N-(3,4-dimethoxy phenyl ethyl)amine.

The base obtained is purified by recrystallisation in methylethylketone.

Melting point: 138° C
Yield: 40%
Empirical formula: $C_{29}H_{39}N_3O_7$
Elementary analysis

|  | C | H | N |
|---|---|---|---|
| Calculated (%) | 64.30 | 7.26 | 7.76 |
| Found (%) | 64.36 | 7.13 | 7.76 |

The derivatives of formula I were studied in conjunction with laboratory animals and showed peripheral, coronary and cerebral vasodilatory properties, as well as antihypertensive properties.

1. Peripheral vasodilatory properties

Administered intra-arterially to an anaesthetised dog not modifying the arterial pressure, the derivatives of formula I are capable of increasing the femoral artery flow in which the injection is carried out (the measurement is effected by means of an electromagnetic flowmeter placed on this artery).

Thus, following the administration of 500 μg/kg/i.a. of derivatives n° 74 0479, 74 0678, 75 0001 and 75 0002, an increase of 120% (for 3 minutes), 226% (for 4.5 mins), 106% (for 7 mins) and 105% (for 8 mins) of femoral artery flow was observed respectively.

2. Coronary vasodilatory properties

Administered to an anaesthetised dog by single intravenous injection, the derivatives of formula I are capable of increasing flow in the anterior interventricular artery, the measurement being effected by means of an electromagnetic flowmeter placed on this artery.

As examples, the derivatives n° 74 0479, 74 0678, 75 0001 and 75 0002, administered respectively in doses of 4 mg/kg/i.v., 2 mg/kg/i.v., 4 mg/kg/i.v. and 4 mg/kg/i.v. cause an increase of the flow in the anterior interventricular artery of 190% (for 40 minutes), 148% (for 8.3 mins), 45% (for 19 mins) and 100% (for 19 mins) respectively.

Furthermore, administered by intravenous perfusion, the derivatives of formula I are capable of increasing the flow and oxygenation of the coronary veinous sinus, the flow of the coronary veinous sinus being measured volumetrically by means of a modified MORAWITZ probe, whilst the oxygen content of the coronary veinous blood is calculated from the rate of hemoglobin saturation measured by hemoreflectometry.

As examples, table I below gives the results obtained.

Thus, the derivatives n° 74 0479, 74 0678 and 75 0001, administered in a dose of 8 mg/kg/i.v., cause an increase in the sub-cortical flow of 58% (for 47 mins), 45% (for 5 mins) and 105% (for 22 mins) respectively.

4. Antihypertensive properties

Compound n° 74 0479, administered in a dose of 100 mg/kg/po to a genetically hypertensive rat, is capable of lowering by 30 mmHg the systolic arterial pressure in 60% of the animals for a duration exceeding 24 hours.

Furthermore, as can be seen from a comparison of the lethal doses given in table II below and the pharmacologically active doses mentioned above, the divergence between the two doses is sufficient to permit the therapeutic use of the derivatives of formula I.

TABLE II

| Number code of derivative tested | Orally (mouse) | | intravenously (mouse) | |
|---|---|---|---|---|
| | Dose administered (mg/kg) | Percentage mortality (%) | Dose administered (mg/kg) | Percentage mortality (%) |
| 74 0678 | — | — | 255 | ≃ 50 |
| 75 0001 | — | — | 580 | ≃ 50 |
| 75 0002 | 2 000 | 30 | 200 | ≃ 50 |
| 74 0479 | 2 250 | 50 | 700 | ≃ 50 |

The pharmacological properties of compound n° 67 350 described in U.S. Pat. No. 3,634,411 and used in human therapy as a vasodilator were compared with the compounds of the invention. The results obtained are given in Table III below.

TABLE III

| Pharmacological test | Manner of adminis. | Dose administered (mg/kg) | | | | | Effect | | | | |
|---|---|---|---|---|---|---|---|---|---|---|---|
| | | 740 479 | 740 678 | 750 001 | 750 002 | 67 350 | 740 479 | 740 678 | 750 001 | 750 002 | 67 350 |
| Acute toxicity (mouse) (DL 50) | p.o. | 2 250 | — | — | 2 000 | 1 000 | 50 % mortality | — | — | 30 % mortality | 50 % mortality |
| | i.v. | 700 | 255 | 580 | 200 | 617 | " | ≃ 50 % mortality | ≃ 50 % mortality | ≃ 50 % mortality | " |
| Peripheral vasodilatory action (increase of femoral flow) | i.a. | 0.5 | 0.5 | 0.5 | 0.5 | 0.5 | + 120 % (3 min.) | + 226 % (4.5 min.) | + 106 % (7 min.) | + 105 % (8 min.) | + 82 % (12 min.) |
| Coronary vasodilatory action increase of flow in the anterior interventricular artery) | i.v. | 4 | 2 | 4 | 4 | 12.5* | + 190 % (40 min.) | + 148 % (8.3 min.) | + 45 % (19 min.) | + 100 % (19 min.) | + 59 % (60 min.) |
| Hypertensive action (vigil SHR rat) | p.o | 100 | — | — | — | 100 | − 60 % (24 h.) | — | — | — | −40 %(4h) −20 %(24h) |

*12.5 mg/kg perfused in 10 min. (1 ml/min)

TABLE I

| Code number of derivative tested | Dose administered by intravenous perfusion (mg/kg) | Increase of flow and oxygenation of the the coronary veinous sinus and duration of effect | |
|---|---|---|---|
| | | Flow | Oxygenation |
| 74 0678 | 12.7 | 65 %  30 min. | 162 %  60 min. |
| 75 0001 | 29 | 88 %  15 min. | 142 %  60 min. |
| 75 0002 | 20 | 124 %  15 min. | 214 %  60 min. |
| 74 0479 | 17.5 | 50 %  15 min. | 132 %  30 min. |

3. Cerebral vasodilatory properties

Administered to an anaesthetised cat by single intravenous injection, the derivatives of formula I are capable of increasing the sub-cortical irrigation measured according to a technique derived from the thermoconductimetric method of SEYLAZ.

It can be seen from this table that the compounds of the invention provide a technical advance over the known vasodilator, since they are distinguished from it by:

a greater, but shorter, peripheral vasodilatory activity;

a much more marked coronary vasodilatory activity; and a more prolonged antihypertensive activity.

Compounds of the invention are indicated in the treatment of coronary, cerebral and peripheral circulatory deficiencies and hypertension.

It would be administered orally in the form of tablets, pills, or gelules containing 20 to 200 mg of active ingredient (1 to 5 per day), in the form of drops containing from 0.25 to 5% of active ingredient (5 to 50 drops - 1 to 3 times a day), parenterally in the form of injectable ampoules containing 10 to 200 mg of active ingredient (1 to 3 per day) and rectally in the form of suppositories containing 20 to 150 mg of active ingredient (1 to 3 per day).

What we claim is:

1. A compound having the formula

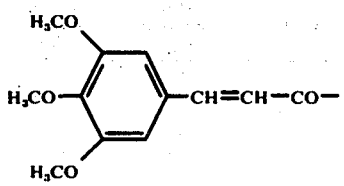

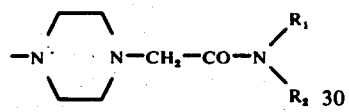

in which $R_1$ is alkyl having one to 4 carbon atoms and $R_2$ is dimethoxyphenylethyl, or

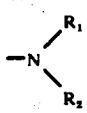

is piperidino, heptamethylenimino or 1,2,3,4-tetrahydro isoquinolino, and the pharmacologically acceptable acid addition salts thereof.

2. A compound as claimed in claim 1, in which $R_1$ is alkyl having one to 4 carbon atoms and $R_2$ is dimethoxyphenylethyl.

3. A compound as claimed in claim 2, in which $R_1$ is methyl and $R_2$ is 3,4-dimethoxyphenylethyl.

4. A compound as claimed in claim 1 in which

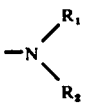

is piperidino.

5. A compound as claimed in claim 1 in which

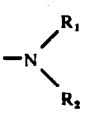

is heptamethylenimino.

6. A compound as claimed in claim 1 in which

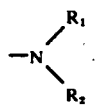

is 1,2,3,4-tetrahydro isoquinolino.

7. A process for preparing a compound having the formula

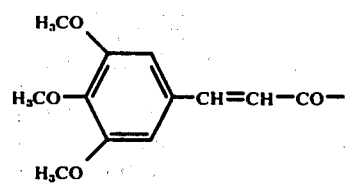

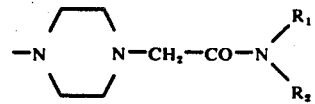

in which $R_1$ is alkyl having one to 4 carbon atoms and $R_2$ is dimethoxyphenylethyl, or

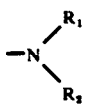

is piperidino, heptamethylenimino or 1,2,3,4-tetrahydro isoquinolino, which comprises reacting a starting compound having the formula

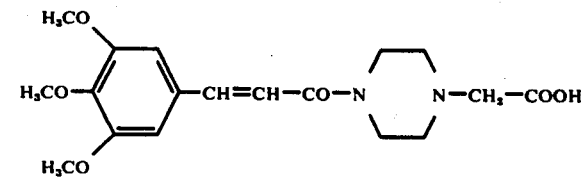

which is a secondary amine having the formula

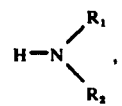

in the presence of butyl chloroformate.

8. A process as claimed in claim 7 in which said starting compound is dissolved in anhydrous tetrahydrofuran, then triethylamine and butyl chloroformate are added to the solution and then said amine is added to the solution.

* * * * *